United States Patent [19]

Dauben et al.

[11] 4,419,287

[45] Dec. 6, 1983

[54] STEREOCONTROLLED SYNTHESIS OF STEROIDAL SIDE CHAINS

[75] Inventors: William G. Dauben; Todd E. Brookhart, both of Berkeley, Calif.

[73] Assignee: The Regents of the University of California, Berkeley, Calif.

[21] Appl. No.: 381,171

[22] Filed: May 24, 1982

Related U.S. Application Data

[63] Continuation of Ser. No. 216,959, Dec. 16, 1980, abandoned.

[51] Int. Cl.$^3$ ................................................ C07J 9/00
[52] U.S. Cl. ................................................ 260/397.1
[58] Field of Search ........................... 260/397.1, 397.2

[56] References Cited

U.S. PATENT DOCUMENTS 3,665,020  5/1972  Marbet ............................ 260/397.2
4,268,453  5/1981  Barner et al. .................... 260/397.5

OTHER PUBLICATIONS

Barry M. Trost et al., J. Org. Chem., vol. 42, No. 11, 1977, pp. 2036-2038.
Barry M. Trost et al., J. Am. Chem. Soc., vol. 100, No. 11, 1978, pp. 3435-3443; vol. 101, No. 15, pp. 4378-4380.
Paul A. Grieco et al., J. Am. Chem. Soc., vol. 101, No. 15, p. 4380-4381, 1979.
Steven R. Schow et al., J. Org. Chem., vol. 44, No. 22, 1979, pp. 3760-3765.
Masato Koreeda et al., J. Org. Chem, 1980, 45, pp. 1172-1174.
Masato Tanabe et al., J. Am. Chem. Soc., 1980, vol. 102, No. 2, pp. 862-863.
Alan M. Krubiner et al., J. Org. Chem, 1966, vol. 31, pp. 24-26; vol. 33, No. 5, 1968, pp. 1715-1718.
Barry B. Snider et al., J. Am. Chem. So., vol. 101, No. 18, 1979, pp. 5283-5293.
Wallis et al., J.A.C.S., vol. 57, PP. 1504-1506 (1935).
Ruzieka et al., Helv. Chim Acta, vol. 18, pp. 986-994 (1935).
Riegel et al., J.A.C.S., pp. 723-724 (1944).
Norman, Vitamin D the Calcium Homeostatic Steroid Hormone, pp. 56-59 (1979).

Primary Examiner—Elbert L. Roberts
Attorney, Agent, or Firm—Majestic, Gallagher, Parsons & Siebert

[57] ABSTRACT

A method for stereospecifically synthesizing a steroidal side chain is disclosed which provides high yield, and which may be utilized with a variety of steroidal starting materials including unprotected, unsaturated steroidal alcohols. The method includes providing a first steroid having an aliphatic chain attached by a carbon-carbon double bond and contacting the first steroid with an aliphatic adduct in the presence of a Lewis acid.

8 Claims, No Drawings

STEREOCONTROLLED SYNTHESIS OF STEROIDAL SIDE CHAINS

The invention described herein was made in the course of, or under, a grant from the National Institute of Health.

This is a continuation of Ser. No. 216,959, filed Dec. 16, 1980, now abandoned.

BACKGROUND OF THE INVENTION

1. Field of the Invention

The present invention relates generally to steroids, and more particularly to the stereocontrolled synthesis of side chains onto tetracyclic steroidal compounds.

2. Prior Art

Steroids are derivatives of a perhydrocyclopentanophenanthrene nucleus which has the structure (including carbon and ring numbering) illustrated below:

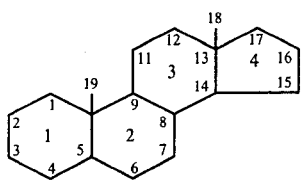

Many biologically active steroids include a substituent group at $C_3$ of the first ring and a side chain at $C_{17}$ of the fourth ring. For example, sterols represent one, extremely abundant, class of steroids which include an alcoholic hydroxyl group at $C_3$ and a branched, aliphatic chain at $C_{17}$.

Among various of the naturally occurring steroid hormones are those including a carbon-carbon double bond between $C_5$ and $C_6$ (for example, pregnenolone) and those which include a carbon-carbon double bond between $C_4$ and $C_5$ (for example, progesterone).

There is considerable interest in synthesizing naturally occurring steroids, novel steroids and derivatives thereof. For example, various procedures have involved the introduction of functionalized steroidal side chains in efforts to synthesize a variety of ecdysones, vitamin D metabolites, and unusual marine sterols.

However, the various syntheses involving steroidal side chains have frequently provided low yields, and/or have involved a number of steps which have increased costs of commercial syntheses of biologically active steroids and their derivatives. Additionally, many of the known efforts towards introducing steroidal side chains have not been stereospecific. Thus, separation of the stereoisomers is required where the ultimate, desired steroid or steroid derivative is one having biological activity.

For example, vitamin $D_3$ is a steroid derivative which may be synthetically prepared from precursors leading to 7-dehydrocholesterol, which is then irradiated by ultraviolet light to produce vitamin $D_3$. However, precursors for vitamin D must have the side chains thereof set so as to define an R stereo configuration in order to be biologically active. Thus, most of the biologically active steroids and their derivatives have continued to be derived from purification of natural sources.

SUMMARY OF THE INVENTION

Accordingly, it is an object of the present invention to provide a method for stereospecifically synthesizing a steroidal side chain in high yield.

It is another object of the present invention that a method for stereospecifically synthesizing a side chain be provided which may be performed directly on an unprotected, unsaturated steroidal alcohol.

These and other objects of the present invention are provided by a method for stereospecifically synthesizing a steroidal side chain comprising the step of providing a first steroid defining a 17 position carbon. An aliphatic chain, defining a 20 position carbon, is attached by a carbon-carbon double bond between the 17 position carbon and a 20 position carbon. The inventive method further comprises the step of contacting the first steroid with an aliphatic adduct in the presence of a Lewis acid to stereospecifically bond the aliphatic adduct to the 20 position carbon and to form a second steroid. The provided first steroid has a Z or an E stereoconfiguration, and the second steroid formed in accordance with the present invention has a stereo configuration corresponding thereto.

In another aspect of the present invention, a compound having the structure

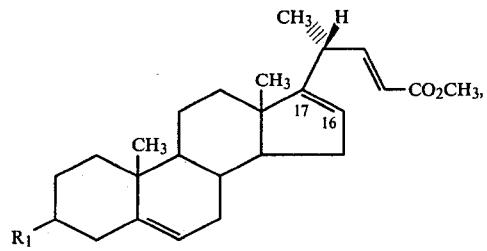

wherein $R_1$ is a hydroxy group or an acetoxy group, is disclosed. This compound may be synthesized in accordance with the inventive method, and the $C_{16}$–$C_{17}$ double bond may be selectively hydrogenated to yield a third steroid. Such a third steroid may then be utilized as a precursor for preparing biologically active steroids and steroid derivatives, such as vitamin D, by known procedures.

DETAILED DESCRIPTION OF THE PREFERRED EMBODIMENTS

The inventive method is for stereospecifically synthesizing a steroidal side chain onto a steroidal starting material, or first steroid, and comprises a providing step and a contacting step. Each step shall now be more particularly described.

PROVIDING STEP

In accordance with the invention a first steroid is provided which includes first, second, third and fourth fused rings and an aliphatic chain which defines a 20 position carbon and which is attached to a 17 position carbon of the fourth ring by a carbon-carbon double bond. The first ring of this steroid defines a three position carbon, which may have a substituent group attached thereto, such as for example —OH, —OMe, —OAC and the like. (As used sometimes throughout, "Me" stands for methyl, "Et" for ethyl and "Ac" for acetyl.) The first steroid has a Z or an E stereo configuration for the carbon-carbon double bond between $C_{17}$ and $C_{20}$. The structure and two isomers of a provided first steroid as just described is generally illustrated below by FIG. I, where R generally represents a substituent group, or may be —H.

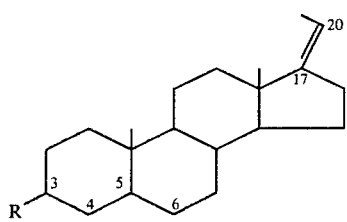

FIG. I (Z isomer)

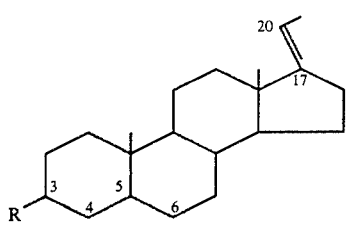

FIG. I (E isomer)

The first steroid defines four, five and six position carbons, and preferably has a carbon-carbon double bond between $C_5$–$C_6$ or between $C_4$–$C_5$.

The aliphatic chain (having the structure =CH—$(CH_2)_n$—$CH_3$) may be branched, but more preferably is unbranched as a branched aliphatic chain will generally result in a slower reaction during the contacting step of the inventive method. The number of carbon atoms in the aliphatic chain (e.g. "n") may vary substantially as desired. That is, n may be chosen from among various integers or may be 0.

Particularly preferred as the first steroid for the providing step are several 17 (20) —Z-pregnene derivatives illustrated by FIGS. IA, IB and IC, below.

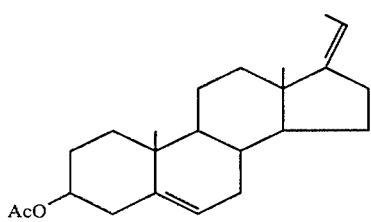

FIG. IA

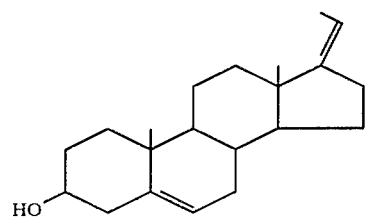

FIG. IB

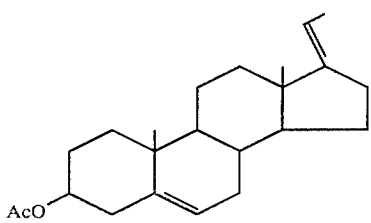

FIG. IC

CONTACTING STEP

The provided first steroid is contacted with an aliphatic adduct in the presence of a Lewis acid which is also a proton scavenger. During the contacting step, the aliphatic adduct reacts with the first steroid, is stereospecifically bonded to the 20 position carbon of the aliphatic chain, and forms a second steroid. The Lewis acid catalyzes the reaction. The contacting is preferably conducted in an organic solvent, more preferably conducted in benzene, toluene or methylene chloride, most preferably conducted in benzene.

A suitable Lewis acid has not only the capacity to take up an electron pair in order to form a covalent bond characteristic of a Lewis acid, but also functions as a proton scavenger. The primary reason for the proton scavenging function of the Lewis acid in the contacting step is to reduce the concentration of hydrogen ions during the contacting step, as the provided first steroid tends to be otherwise destroyed during the reaction.

Suitable Lewis acids include ethylaluminum dichloride, diethylaluminum chloride, and mixtures thereof. The most preferred Lewis acid in practice of the present invention is diethylaluminum chloride. A Lewis acid without a significant proton scavenging function, such as aluminum chloride, may be admixed with the one (or more) suitable Lewis acid if desired.

A suitable aliphatic adduct for use in the inventive method includes an electron deficient carbon, more particularly an electron deficient carbon which is part of a carbonyl moiety or a propargylogous derivative of a carbonyl containing compound. For example, the aliphatic adduct may be selected from various carbonyl compounds, such as esters and aldehydes, or from propargylogous, or dehydrovinylogous, derivatives thereof, such as propiolate esters. The electron deficient carbon is bonded to the $C_{20}$ of the aliphatic chain.

Where the aliphatic adduct has more than one electron deficient carbon (such as a propargylous derivative of a carbonyl containing compound), the electron deficient carbon which stereospecifically bonds to the 20 position carbon of the aliphatic chain will be that carbon atom of the triply-bonded pair of carbon atoms which is more distal from the carbonyl carbon. Thus, for example where the aliphatic adduct is a propiolate ester, it is the β carbon which will bond to the 20 position carbon of the first steroid's aliphatic chain.

Substantially all the second steroid formed has a stereo configuration which corresponds to the first steroid. The second steroid also includes a carbon-carbon double bond between the $C_{16}$ and $C_{17}$ of the fourth ring. This $C_{16}$–$C_{17}$ double bond may be selectively hydrogenated to form a third steroid, as shall be more fully discussed hereinafter.

The inventive method shall now be illustrated by Examples I–V, below.

Unless otherwise noted, materials were obtained from commercial suppliers and were used without further purification. Benzene and toluene were distilled from sodium/benzophenone prior to use. Melting points are uncorrected. IR spectra were determined with a Perkin-Elmer Model 281 infrared recording spectrophotometer. Specific rotations were determined with a Perkin-Elmer Model 24 Polarimeter. $^1$H-NMR spectra were determined on the following spectrometers: Varian T-60, Varian EM 390, or UCB 250 (a superconducting, 250 MHz, FT instrument). $^{13}$C-NMR spectra were measured at 25.14 MHz with a Nicolet TT-23 spectrometer. Chemical shifts are expressed in ppm downfield from internal tetramethylsilane. Significant ¹H-NMR data are tabulated in order: multiplicity (s, singlet; d, doublet; t, triplet; q, quartet; m, multiplet), number of protons, coupling constant(s) in Hertz. Mass spectra were obtained with Atlas MS-12 and consolidated 12-110B mass spectrometers. Mass spectral data are tabulated as m/e (intensity expressed as percent of total ion current).

EXAMPLE I

Preparation of Methyl (20R, 22E)-3β-Acetoxychola-5,16,22-trienate

To a solution of 500 mg of first steroid, having the structure illustrated by FIG. IA, above, (prepared by the method of Drefahl et al., Chem.Ber, 98, (1965) 604) and 147 mg (1.2 eq.) of methyl propiolate in 10 mL of benzene under an atmosphere of nitrogen was added dropwise 1.79 mL (2.0 eq.) of a 25% solution of diethyl-aluminum chloride in toluene. The reaction mixture was stirred at room temperature for 24 h, then poured into 50 mL of a 5% aqueous sodium bicarbonate solution and extracted with ether. The organic layer was then washed with an aqueous saturated salt solution, dried (MgSO₄) and the solvent removed under reduced pressure to afford 590 mg (95%) of a slightly yellow solid, which was recrystallized from methanol to produce second steroid, methyl (20R,22E)-3β-Acetoxychola-5,16,22-trienate, having the structure illustrated by FIG. IIA, below, as a white solid, mp 129°-130° C. $[α]_D$(CHCl₃): -24.0°; IR (CHCl₃): 1720, 1650, 1020, and 980 cm⁻¹; ¹H-NMR (CDCl₃): δ6.90 (dd, 1H, J=8, 16), 5.80 (dd, 1H, J=1.5, 16), 5.40 (m, 2H), 3.70 (s, 3H), 3.00 (qt, 1H, J-7, 8), 1.17 (d, 3H, J=7), 1.00 (s, 3H), 0.80 (s, 3H); ¹³C-NMR (CDCl₃): δ170.1, 167.0, 156.9, 153.4, 139.9, 123.9, 122.2, 118.8, 73.7, 57.2, 51.1, 50.5, 46.9, 38.0, 36.8, 36.7, 35.3, 34.7, 31.4, 31.0, 30.3, 27.6, 21.1, 20.6, 19.4, 19.0, 16.2. Mass spectrum: m/e 366 (4.96, parent—CH₃CO₂H, base), 253 (4.71).

Anal. Calcd for C₂₇H₃₈O₄: C, 76.02; H, 8.98. Found: C, 76.10; H, 8.99.

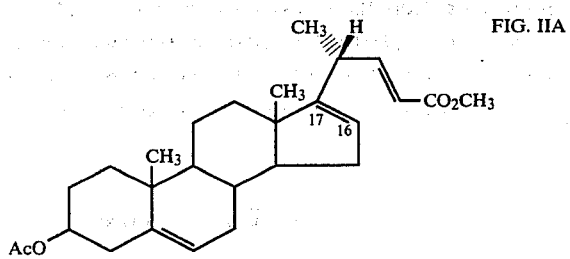

FIG. IIA

EXAMPLE II

Preparation of Methyl (20R,22E)-3β-Hydroxychola-5,16,22-trienate

To a solution of 1.00 g of first steroid, having the structure illustrated by FIG. IB, above, (prepared by the method of Drefahl et al, supra) and 318 μL (1.2 eq.) of methyl propiolate in 25 mL of benzene at 5° C. under an atmosphere of nitrogen was added dropwise 6.15 mL (3 eq.) of a 25% solution of diethylaluminum chloride in toluene. The reaction mixture was allowed to warm to room temperature and was stirred for 24 h, then poured into 100 mL of a 5% aqueous sodium bicarbonate solution and extracted with ether. The organic layer was then washed with an aqueous saturated salt solution, dried (MgSO₄) and the solvent removed under reduced pressure to afford a 95% yield of second steroid, methyl (20R,22E)-3β-Hydroxychola-5,16,22-trienate, having the structure illustrated by FIG. IIB, below, which was recrystallized from methanol to produce a white solid, mp 80°-90° C. IR (CHCl₃): 3600, 3450 (br), 1715, 1650, 1040, 1020, and 980 cm⁻¹; ¹H-NMR (CDCl₃): δ6.90 (dd, 1H, J=8, 16), 5.80 (dd, 1H, J=1.5, 16), 5.40 (m, 2H), 3.70 (s, 3H), 3.0 (qt, 1H, J=7,8) 1.17 (d, 3H, J=7), 1.00 (s, 3H), and 0.80 (s, 3H); ¹³C-NMR (CDCl₃): δ167.2, 157.0, 153.6, 141.2, 123.9, 121.1, 118.7, 71.4, 57.2, 51.2, 50.6, 47.0, 42.2, 37.2, 36.6, 35.3, 34.8, 31.4 (2 carbons), 31.0, 30.4, 20.6, 19.4, 19.1, 16.2: Mass spectrum: m/e 384 (0.44, parent), 271 (4.48, base).

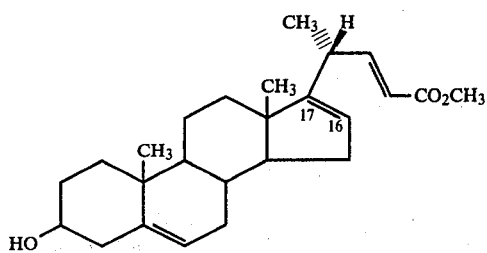

FIG. IIB

Due to water of hydration the melting point was wide, and the analysis corresponded to the molecular formula of the FIG. IIB second steroid plus 0.50 equivalents of water.

To confirm the identity of the FIG. IIB second steroid, 180 mg was dissolved in 2 mL of acetic anhydride and heated on a steam bath for 2 h then cooled to room temperature. The solid was collected and recrystallized from methanol to afford 170 mg (85%) of the FIG. IIA second steroid, mp 129°-130° C. The melting point of a mixture of this material and the synthesized FIG. IIA second steroid from Example I showed no depression.

EXAMPLE III

Preparation of Methyl (20S,22E)-3β-Acetoxychola-5,16,22-trienate

To a solution of 490 mg of first steroid, having the structure illustrated by FIG. IC, above, (prepared by the method of Butenandt et al., Helv. Chim. Acta, 11 (1938) 1313) and 0.155 mL (1.2 eq.) of methyl propiolate in 10 mL of benzene under an atmosphere of nitrogen was added dropwise 1.79 mL (2.0 eq.) of a 25% solution of diethylaluminum chloride in toluene. The reaction mixture was stirred at room temperature for 5 days, then poured into 50 mL of a 5% aqueous sodium bicarbonate solution and extracted with ether. The organic layer was then washed with an aqueous saturated salt solution, dried (MgSO₄) and the solvent removed under reduced pressure to afford a mixture of the starting first steroid and product second steroid, illustrated by FIG. IIC, below. The mixture was chromatographed on silica with a 10% ether-hexane mixture as the eluent. The less polar fraction contained 297 mg (reaction 38% complete) of starting first steroid, while the more polar fraction contained 226 mg (94.6% based on recovered starting material) of product second steroid. The product was recrystallized from methanol to produce a white solid, mp 121°-122° C. $[α]_D$(CHCl₃): -66.9°; IR (CHCl₃): 1720, 1650, 1030, and 980 cm⁻¹; ¹H-NMR (CDCl₃)δ6.92 (dd, 1H, J=8, 16), 5.80 (dd, 1H, J=1.5, 16), 5.43 (m, 2H), 3.75 (s, 3H), 3.04 (qt, 1H J=7, 8), 1.22 (d, 3H, J=7), 1.08 (s, 3H), 0.81 (s, 3H); $^{13}$C-NMR (CDCl$_3$): δ170.3, 167.2, 156.2, 153.4, 139.7, 123.8, 122.3, 119.0, 73.7, 56.8, 51.3, 50.3, 47.0, 38.0, 36.8, 36.6, 35.0, 34.8, 31.3, 31.1, 30.3, 27.6, 21.3, 20.6, 19.8, 19.1, 16.1. Mass spectrum: m/e 366 (9.20, parent-CH$_3$CO$_2$H, base), 351 (2.89), 253 (2.78).

Anal. Calcd for C$_{27}$H$_{38}$O$_4$: C, 76.02; H, 8.98. Found: C, 75.86; H, 8.95.

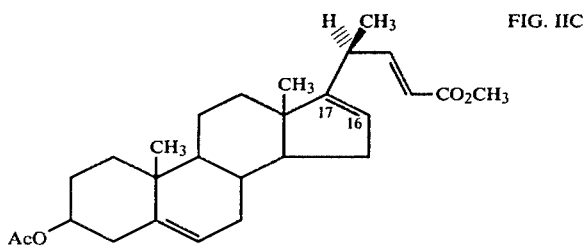

FIG. IIC

EXAMPLE IV

Preparation of Methyl (20R, 22E)-3-Methoxy-19-norchola-1,3.5(10),16,22-pentaenate A first steroid having the structure illustrated by FIG. ID, below, was prepared by the method of Krubiner and Oliveto, J.Org.Chem, 31 (1966) 24. To a solution of 222 mg of the FIG. ID first steroid and 6.66 μL (1.0 eq.) of methyl propiolate in 10 mL of benzene under an atmosphere of nitrogen was added dropwise 0.92 mL (2.0 eq.) of a 25% solution of diethylaluminum chloride in toluene. The reaction mixture was stirred at room temperature for 24 h, then poured into 50 mL of a 5% aqueous sodium bicarbonate solution and extracted with ether. The organic layer was then washed with an aqueous saturated salt solution, dried (MgSO$_4$) and the solvent removed under reduced pressure to afford the second steroid product, illustrated by FIG. IID, below, in 90% yield, which was recrystallized from methanol to produce a white solid, mp 83°-84° C. IR (CHCl$_3$): 1710, 1650, 1020, and 980 cm$^{-1}$; $^1$H-NMR (CDCl$_3$): δ6.90 (dd, 1H, J=8, 16), 5.80 (dd, 1H, J=1.5, 16), 5.4 (m, 1H), 3.72 (s, 3H), 3.70 (s, 3H), 3.0 (qt, 1H, J=7, 8), 1.20 (d, 3H, J=7), 0.80 (s, 3H); $^{13}$C-NMR (CDCl$_3$) δ167.3, 157.6, 157.4, 153.7, 138.0, 133.0, 125.9, 124.0, 118.9, 114.0, 111.5, 75.7, 56.6, 55.2, 51.3, 47.6, 44.4, 37.5, 35.5, 35.0, 30.9, 29.7, 27.7, 26.5, 19.7, 16.5.

Anal. Calcd for C$_{25}$H$_{32}$O$_3$: C, 78.91; H, 8.48. Found: C, 79.13; H, 8.57.

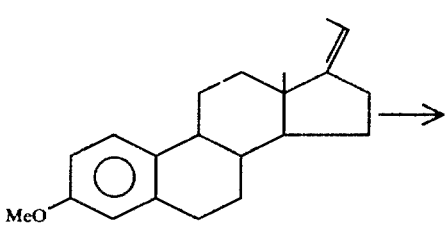

FIG. ID

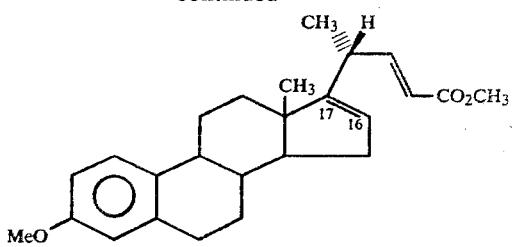

FIG. IID

The inventive method may further comprise the step of selectively hydrogenating the C$_{16}$-C$_{17}$ of the second steroid to produce a third steroid. The side chain of the third steroid may then be lengthened by various conventional procedures known to the art, for example in order to produce vitamin D and various of its derivatives. Such selective hydrogenating is illustrated by Example V, below.

EXAMPLE V

Preparation of Methyl (20R)-3β-Acetoxychola-5-enate

A solution containing 200 mg of the second steroid, illustrated by FIG. IIA of Example I, above, and 100 mg of 5% palladium on calcium carbonate in 12 mL of ethyl acetate was stirred under an atmosphere of hydrogen at ambient pressure until two equivalents had been taken up. The absorption of hydrogen at this point stopped. The reaction mixture was filtered and the solvent removed under reduced pressure to afford a 98% yield of a third steroid, illustrated by FIG. III, below, which was recrystallized from methanol to produce a white solid, mp 162°-163° C. (Vanderah and Djerass report 159°-161° C., J. Org.Chem., 93 (1978) 1442). The spectral data from this compound and an independently synthesized sample (by the method of Butenandt, supra) were identical in every detail, also the melting point of a mixture of these samples exhibited no depression.

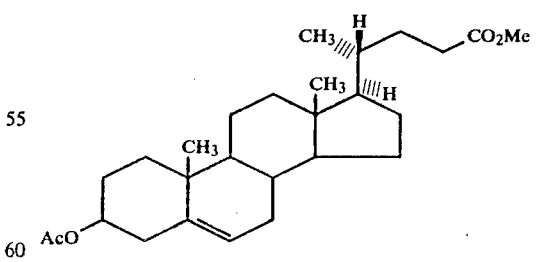

FIG. III

In summary, the present invention provides a direct method for easily, and in high yield, stereospecifically synthesizing a steroidal side chain onto a wide variety of steroidal starting materials.

We claim:

1. A compound having the structure

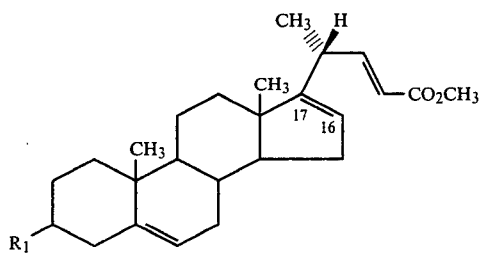

wherein $R_1$ is —OH or —OCCH$_3$.
$$\underset{O}{\overset{\|}{}}$$

2. A method for stereospecifically synthesizing a steroidal side chain comprising:
providing a steroidal starting material defining a Z or an E stereo configuration, a 20 position carbon, and having the structure

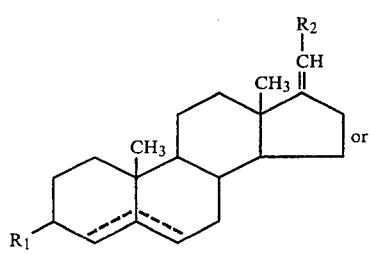

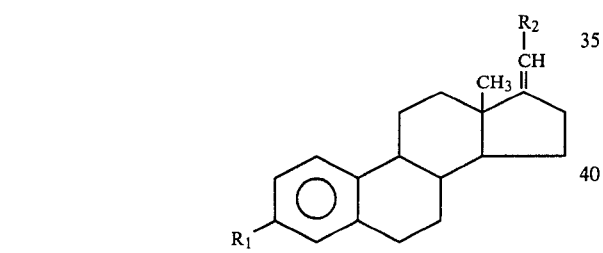

wherein R, is hydrogen, —OH, —OCH$_3$ or

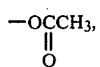

$R_2$ is an alkyl group, and the dotted lines indicate the presence or absence or bonds;
reacting the steroidal starting material with a propiolate ester in the presence of ethylaluminum dichloride, diethylaluminum chloride or mixtures thereof, the reacting introducing the propiolate ester as a steroidal side chain onto the steroidal starting material at the 20 position carbon while retaining the stereo configuration thereof.

3. The method as in claim 2 wherein the propiolate ester is methyl propiolate.

4. The method as in claim 2 wherein $R_1$ is —OH, —OCH$_3$ or

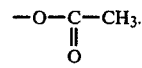

5. The method as in claim 2 wherein $R_2$ is —CH$_3$.

6. The method as in claim 2 wherein the reacting is conducted in an organic solvent in the presence of diethylaluminum chloride.

7. The method as in claim 3 wherein:
a reaction product formed in the reacting has the structure

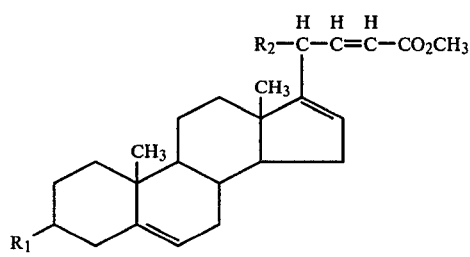

8. A method for synthesizing a steroidal compound useful as a precursor of biologically active steroids comprising:
providing an initial steroid having the structure

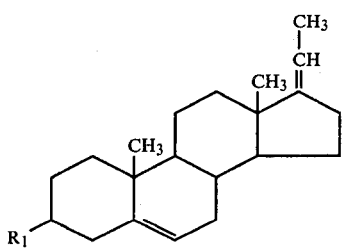

wherein $R_1$ is —OH, —OCH$_3$ or

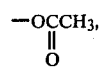

the initial steroid having a Z stereo configuration;
stereocontrolledly reacting the initial steroid with methyl propiolate in the presence of diethylaluminum chloride; and,
selectively hydrogenating a reaction product of the reacting to form a resultant steroid having a stereo configuration corresponding to the initial steroid and having the structure

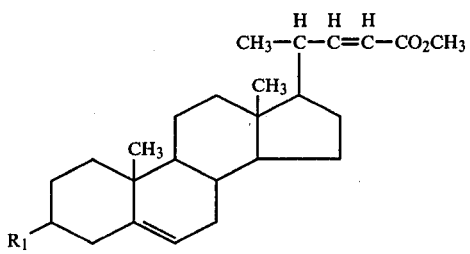

* * * * *

UNITED STATES PATENT AND TRADEMARK OFFICE
CERTIFICATE OF CORRECTION

PATENT NO. : 4,419,287
DATED : December 6, 1983
INVENTOR(S) : William G. Dauben and Todd E. Brookhart It is certified that error appears in the above-identified patent and that said Letters Patent is hereby corrected as shown below:

Column 3, line 38, please delete "and IC".

Column 3, lines 60-68, please delete the legend "FIG IC and structure".

Signed and Sealed this

Thirty-first Day of July 1984

[SEAL]

Attest:

GERALD J. MOSSINGHOFF

Attesting Officer

Commissioner of Patents and Trademarks